United States Patent [19]

Hussain et al.

[11] Patent Number: 5,704,297
[45] Date of Patent: Jan. 6, 1998

[54] DRY POWDER COMPOSITION OF HYDROXYETHYL STARCH SUITABLE FOR RECONSTITUTION

[75] Inventors: Munir Alwan Hussain, Wilmington, Del.; Raghunath Srinivas, Barington, Ind.; Lei-Shu Wu, Wilmington, Del.

[73] Assignee: The DuPont Merck Pharmaceutical Company, Wilmington, Del.

[21] Appl. No.: 652,034

[22] Filed: Feb. 6, 1991

[51] Int. Cl.$^6$ .............................. C08L 3/08; A61K 9/08; A61K 31/72

[52] U.S. Cl. .................... 106/215.5; 424/400; 424/488

[58] Field of Search .................. 106/210, 213, 106/214, 171, 215.5; 424/488, 400

[56] References Cited

U.S. PATENT DOCUMENTS

| | | |
|---|---|---|
| 3,034,911 | 5/1962 | Mikee et al. .............................. 106/214 |
| 3,523,938 | 8/1970 | Hershenson et al. |
| 3,951,949 | 4/1976 | Hamuro et al. .......................... 106/213 |
| 3,960,584 | 6/1976 | Sauage ................................. 106/197.1 |
| 4,076,547 | 2/1978 | Lester et al. ............................ 106/210 |
| 4,306,059 | 12/1981 | Yokobayashi et al. .................. 106/213 |
| 4,435,217 | 3/1984 | House ..................................... 106/171 |
| 4,798,824 | 1/1989 | Belzer et al. |
| 4,873,230 | 10/1989 | Belzer et al. |
| 4,879,283 | 11/1989 | Belzer et al. |

Primary Examiner—David Brunsman

[57] ABSTRACT

The present invention relates to a dry powder composition of hydroxyethyl starch suitable for reconstitution and comprising hydroxyethyl starch of a molecular weight of up to about 2,000,000, a degree of substitution of from about 0.4 to about 0.7, and containing less than about 0.5 parts by weight of ethylene glycol per 100 parts of the hydroxyethyl starch, the hydroxyethyl starch comprising from about 4% to about 40% by weight of the composition. The composition includes at least one soluble component in addition to the hydroxyethyl starch chosen from dextrose, lactose or mannitol.

6 Claims, No Drawings

DRY POWDER COMPOSITION OF HYDROXYETHYL STARCH SUITABLE FOR RECONSTITUTION

BACKGROUND OF THE INVENTION

Colloids are frequently used in the resuscitation of hypovolemic patients with shock. Potential benefits of maintaining or increasing plasma colloid osmotic pressure include the rapid restoration of the circulating plasma volume and the avoidance of excessive fluid accumulation, particularly in the lung U.S. Pat. No. 3,523,938 issued Aug. 11, 1970, for Starch Plasma Expanders and Process of Preparation describes the preparation and use of hydroxyethyl starch as a plasma volume expander. HESPAN is a plasma volume expander, made as described in U.S. Pat. No. 3,523,938 and currently sold by E. I. du Pont de Nemours and Company, and which uses a fraction of hydroxyethyl starch known as hetastarch. Hetastarch, synthesized by the hydroxyethylation of polysaccharides, contains polymers of a wide range of sizes, 90% of which have a molecular weight of between about 10,000 and 1,000,000 and has a number average molecular weight of about 69,000.

Average molecular weight and molecular weight distribution are useful parameters in defining heterogeneous polymers such as hydroxyethyl starch. Polymer molecular weights are defined several different ways depending on the particular needs.

The number average molecular weight is the most useful term for the clinician concerned with oncotic pressures. The oncotic pressure of hydroxyethyl starch is related to the number of macromolecules in solution and has been measured as 30 mm mercy. Oncotic pressures for various hydroxyethyl starches have been reported. The number average molecular weight is defined as the number of molecules in the fraction having a specific molecular weight times the molecular weight divided by the number of molecules in the fraction. As mentioned before, hetastarch has been synthesized with a number average molecular weight of about 69,000.

The weight average molecular weight is useful to the chemist in defining the polymer resulting from a synthetic process. It is defined as the summation of the weights of individual fractions times the molecular weight of the species within the fractions divided by the sums of the weights of the individual fractions.

Historically, gel permeation chromatography has been used to determine molecular weight distribution and to estimate molecular weight. The molecular weight ranges from 180 for one glucose unit to well over one million for the largest polymer molecule. The distribution of molecules for hetastarch is such that at least 80% of the molecules have a molecular weight between ten thousand and two million. For hetastarch the average molecular weight by gel permeation chromatography is approximately 450,000.

Various hydroxyethyl starch fractions with possibly varying characteristics are used for different purposes. As described, hetastarch is generally used for plasma volume expansion. Pentastarch, as described in U.S. Pat. No. 4,873,230, is used for leukophoresis. This fraction has a molecular weight of from about 150,000 to about 350,000, degree of substitution of from abut 0.4 to about 0.7, and is substantially free of ethylene glycol, ethylene chlorohydrin, sodium chloride and acetone.

An additional fraction, as described in U.S. Pat. No. 4,798,824 issued Jan. 17, 1989, is intended for use in a perfusate for the preservation of organs or in a solution for the preservation of organs, as described in U.S. Pat. No. 4,879,283 issued Nov. 7, 1989. This fraction has a molecular weight of from about 150,000 to about 350,000, a degree of substitution of from about 0.4 to about 0.7, being substantially free of ethylene glycol, ethylene chlorohydrin, sodium chloride and acetone, and being substantially free of hydroxyethyl starch having a molecular weight of less than about 50,000.

While specific fractions may be preferred for specific uses, use of the different fractions can be interchanged in some cases.

All of the current hydroxyethyl starch products are manufactured as solutions. A dry powder composition would be desirable as it would reduce costs with regard to shipping and storage as well as providing additional advantages.

SUMMARY OF THE INVENTION

The present invention relates to a dry powder composition of hydroxyethyl starch suitable for reconstitution and comprising hydroxyethyl starch of a molecular weight of up to about 2,000,000, a degree of substitution of from about 0.4 to about 0.7, and containing less than about 0.5 parts by weight of ethylene glycol per 100 parts of the hydroxyethyl starch, the hydroxyethyl starch comprising from about 4% to about 40% by weight of the composition. The composition includes at least one soluble component in addition to the hydroxyethyl starch.

The dry powder composition can be used for the preparation of formulations requiring hydroxyethyl starch and can be reconstituted just prior to use thereby reducing cost with regard to shipping and storage.

Specific fractions of hydroxyethyl starch can be used for the dry powder composition, depending on the final solution desired and its purpose.

DETAILED DESCRIPTION OF THE INVENTION

The solution rate of hydroxyethyl starch is slow. It has been found that mixing the hydroxyethyl starch with at least one soluble component, namely dextrose, lactose, mannitol or sodium chloride, enhances the dissolution rate so that the dry powder composition dissolves in about 6 minutes to about 8 minutes. The use of dextrose is preferred. By reconstituting the dry powder composition just prior to use, cost is reduced with regard to shipping and storage. Moreover, a dry powder composition would obviate the need for different size solutions, namely 125 ml, 500 ml, 1 liter, etc. which can be made as needed. The dry powder composition would also be useful in disaster or crisis situations. The dry powder composition can also be packaged by conventional powder fill equipment.

The feasibility of developing a dry powder formulation to improve the reconstitution rate of hydroxyethyl starch was investigated. Two approaches were studied.

(I) Mixing the hydroxyethyl starch with additives geometrically to separate the hydrxoyethyl starch particles and to enhance the wetting and dispersion during its reconstitution.

(II) Lyophilizing solutions of hydroxyethyl starch in the presence of additives (dextrose, sodium chloride, lactose or mannitol) to change the powder matrix properties and to enhance the reconstitution rate of pentastarch.

The reconstitution of the powder from the various preparations was conducted by placing 450 ml of water or saline solution into a 500 ml intravenous administration bottle containing pre-weighed powder which would make 10% pentastarch solution after reconstitution. The bottles were shaken using a horizontal shaker with two inches shaking distance, at 168 shakes/minute.

The evaluation was rated on a scale of 1 to 6.

1: All the powder dissolved in 6 minutes,
2: All the powder dissolved in 8 minutes,
3: All the powder dissolved in 10 minutes,
4: 5% remained undissolved at 6 minutes and all dissolved in 12 minutes,
5: 10% remained undissolved at 6 minutes and all dissolved in 14 minutes,
6: 25% remained undissolved at 6 minutes and 5% remained undissolved at 16 minutes.

The results are summarized as follows:

|  |  | Rating |
|---|---|---|
| Preparation A: | Lyophilized powder from a solution of 10% pentastarch, 5% dextrose and 2% glycerol, is a white, hard, and porous cake. | 4 |
| Preparation B: | Lyophilized powder from a solution of 10% pentastarch, 0.9% sodium chloride and 0.5% glycerol, is a white, crispy, and porous cake. | 6 |
| Preparation C: | Lyophilized powder from a solution of 10% pentastarch and 0.5% glycerol, is a white, fluffy, porous cake. | 3 |
| Preparation D: | Lyophilized powder from a solution of 40% pentastarch and 20% dextrose, is a clear, glassy chip. | 6 |
| Preparation E: | Lyophilized powder from a solution of 40% pentastarch and 3.6% sodium chloride, is a mixture of glassy and porous white cake. | 5 |
| Preparation F: | Lyophilized powder from a solution of 40% pentastarch and 2% glycerol, is a dense white, and crispy cake with no visible pore. | 5 |
| Preparation H: | A geometric mixture of pentastarch and dextrose. | 2 |
| Preparation H': | Same as preparation H; however, spray dried pentastarch instead of drum dried being used. | 2 |
| Preparation M: | A powder mixture of pentastarch and dextrose mixed using ½ quart V-blender, is a white free flowing powder. | 1 |
| Preparation M': | Same preparation as M; however, spray dried pentastarch instead of drum dried being used. | 2 |
| Preparation N: | A powder mixture of pentastarch and sodium chloride mixed using ½ quart V-blender, is a white free flowing powder. | 5 |
| Preparation N': | Same preparation as N; however, spray dried pentastarch instead of drum dried being used. | 5 |
| Preparation O: | A powder mixture of pentastarch, dextrose, and sodium chloride using ½ quarter V-blender, is a white free flowing powder. | 2 |
| Preparation O': | Same preparation as O; however, spray dried pentastarch instead of drum dried being used. | 3 |
| Control: | Reconstitution: 90% Remained undissolved at 5 minutes. | 5 |

A geometric powder mixture of pentastarch and dextrose gave a promising result for improving the dissolution rate of the pentastarch. This is a simple and straight forward method and the powder mixture provides a faster reconstitution rate in the hospital as well as eases the in-house preparation of pentastarch solution. The powder mixtures of pentastarch and dextrose, by using a small scale V-blender, showed a fast reconstitution rate also. This demonstrated that it is feasible to be scaled up and still keep the beneficial powder properties.

An example of a suitable formulation is as follows:

| Ingredient | Amount |
|---|---|
| Pentastarch | 50 grams |
| Mannitol | 0–10 grams |
| Sodium chloride | 0–10 grams |
| Dextrose | 0–40 grams |
| Water for injection | Q.S to 500 ml |

What is claimed is:

1. A dry powder composition comprising hydroxyethyl starch of a molecular weight of up to about 2,000,000 daltons, a degree of substitution of from about 0.4 to about 0.7 and containing less than about 0.5 parts by weight of ethylene glycol per 100 parts of the hydroxyethyl starch, and at least one water soluble component selected from dextrose, lactose, and mannitol, and characterized in that the powder dissolves within 8 minutes when 450 ml of water and sufficient powder to provide a 10% hydroxyethyl starch solution are placed in a 500 ml bottle and the bottle is shaken using a horizontal shaker with two inches shaking distance at 168 shakes per minute.

2. The dry powder composition of claim 1 wherein the water soluble component is dextrose.

3. The dry powder composition of claim 1 wherein the hydroxyethyl starch has a molecular weight of from about 150,000 daltons to about 350,000 daltons and is substantially free of ethylene glycol, ethylene chlorohydrin, sodium chloride and acetone.

4. The dry powder composition of claim 3 wherein the water soluble component is dextrose.

5. A dry powder composition comprising hydroxyethyl starch of a molecular weight of from about 150,000 to about 350,000, a degree of substitution of from about 0.4 to about 0.7, being substantially free of ethylene glycol, ethylene chlorohydrin, sodium chloride and acetone, and being substantially free of hydroxyethyl starch having a molecular weight less than 50,000, and at least one water soluble component selected from dextrose, lactose, and mannitol, and characterized in that the powder dissolves within 8 minutes when 450 ml of water and sufficient powder to provide a 10% hydroxyethyl starch solution are placed in a 500 ml bottle and the bottle is shaken using a horizontal shaker with two inches shaking distance at 168 shakes per minute.

6. The dry powder composition of claim 5 wherein the water soluble component is dextrose.

\* \* \* \* \*